United States Patent [19]

Krasner

[11] Patent Number: 4,802,853

[45] Date of Patent: * Feb. 7, 1989

[54] METHOD AND APPARATUS FOR PRESERVING AND REIMPLANTING A TOOTH

[75] Inventor: Paul R. Krasner, Pottstown, Pa.

[73] Assignee: Biological Rescue Products, Inc., Pottstown, Pa.

[*] Notice: The portion of the term of this patent subsequent to Aug. 25, 4004 has been disclaimed.

[21] Appl. No.: 87,206

[22] Filed: Aug. 20, 1987

Related U.S. Application Data

[63] Continuation-in-part of Ser. No. 880,088, Jun. 30, 1986, Pat. No. 4,689,014.

[51] Int. Cl.$^4$ .............................................. A61C 5/00
[52] U.S. Cl. .................................... 433/215; 433/229; 206/83
[58] Field of Search .................. 433/215, 229, 175; 206/63.5, 83, 368, 369, 438, 222, 570, 603, 583, 523

[56] References Cited

U.S. PATENT DOCUMENTS

| | | | |
|---|---|---|---|
| 987,162 | 3/1911 | Oglesby et al. | 206/583 |
| 1,078,431 | 11/1913 | Grier | 206/83 |
| 1,664,419 | 4/1928 | Jackman | 433/77 |
| 2,444,294 | 6/1948 | Jones | 206/83 |
| 2,553,232 | 5/1951 | Beyer | 206/63.5 |
| 2,598,136 | 5/1952 | Schmitz | 206/583 |
| 2,699,780 | 1/1955 | Rudnick et al. | 206/63.5 |
| 2,711,021 | 6/1955 | Parker | 433/175 |
| 2,769,193 | 11/1956 | Jackson | 206/83 |
| 2,971,637 | 2/1961 | Simons | 206/369 |
| 2,973,767 | 3/1961 | Cohen | 206/83 |
| 3,248,167 | 4/1966 | Friedman | 206/369 |
| 3,255,871 | 6/1966 | Butler | 206/438 |
| 3,337,042 | 8/1967 | Bergendal et al. | 206/63.5 |
| 3,337,957 | 8/1967 | Reed | 433/215 |
| 3,360,122 | 12/1967 | Ruckert | 206/63.5 |
| 3,435,946 | 4/1969 | Sobek et al. | 206/523 |
| 3,765,564 | 10/1973 | Persson | 433/25 |
| 3,874,082 | 4/1975 | Stein | 433/228.1 |
| 4,054,220 | 10/1977 | Rosenstein | 206/523 |
| 4,101,031 | 7/1978 | Cromie | 206/438 |
| 4,172,128 | 10/1979 | Thiele et al. | 433/173 |
| 4,203,217 | 5/1980 | Kurer | 433/220 |
| 4,327,060 | 4/1982 | Nisii | 206/369 |
| 4,360,342 | 11/1982 | Salvo | 433/172 |
| 4,443,197 | 4/1984 | Fusayama | 433/217 |
| 4,494,652 | 1/1985 | Nelson et al. | 206/63.5 |

FOREIGN PATENT DOCUMENTS 2432290 1/1976 Fed. Rep. of Germany ...... 206/222

OTHER PUBLICATIONS

"Milk and Saliva as Possible Storage Media . . .", Leif Blomlöf, Swedish Dental *Journal,* vol. 5, Supp. No. 8, pp. 1'4 26 (1981).

"Periodontal and Pulpal Healing of Monkey Incisors . . .", J. O. Andreasen et al., *Int. J. Oral Surgery,* vol. 7, pp. 104–112 (1978).

"Effect of Storage in Media With Different Ion Strengths . . .", L. Blomlöf et al., vol. 89, pp. 180–187 (1981).

*Primary Examiner*—John J. Wilson
*Attorney, Agent, or Firm*—William H. Eilberg

[57] ABSTRACT

A method and apparatus are disclosed for saving an exarticulated tooth. The tooth is grasped by its crown, so as not to harm the periodontal membrane. In one embodiment, the tooth is placed in a net which is attached to a basket. The net and basket are immersed in a modified saline solution which preserves the cells of the periodontal membrane. The solution is held in a container which accommodates the net and basket. The container is closed, and the tooth and patient are taken to a dentist. The dentist removes the lid of the container, and lays the lid on a table or other surface, so that the sponge faces upward. The dentist then lifts the basket, with the tooth, out of the solution, and inverts the net so that the tooth falls out onto the sponge. The dentist then grasps the tooth with a forceps and reimplants it in the patient's mouth. In other embodiments, the net is omitted, and is replaced by padding in the container which protecgts the tooth. In still another embodiment, there is a net but no basket, and the net remains within the container. In another embodiment, the solution is stored in a bag which is held within the container lid. A knife edge punctures the bag when the lid is unscrewed. In yet another embodiment, the tooth is stored in a pouch of water-impermeable material and removed immediately before reimplantation.

16 Claims, 5 Drawing Sheets

_Fig. 6_

_Fig. 7_

METHOD AND APPARATUS FOR PRESERVING AND REIMPLANTING A TOOTH

CROSS-REFERENCE TO PRIOR APPLICATION

This is a Continuation-in-Part of U.S. patent application Ser. No. 880,088, filed June 30, 1986.

BACKGROUND OF THE INVENTION

This invention discloses a method and related apparatus for saving a tooth which has been exarticulated, or knocked out.

Exarticulation of a tooth, also known as an avulsion, occurs when the entire tooth is forcefully and completely knocked out of its socket. Tooth exarticulation is quite common, especially among children. Exarticulation can result from falls, violence, or other causes. It is possible to save an exarticulated tooth, but only if the proper procedures are followed. Due to public ignorance, these procedures are seldom observed. When the exarticulated tooth is brought to a dentist, it is often too late to save the tooth, because the cells of the periodontal membrane have died.

All teeth have two main components, namely the crown and the root. The crown is the portion of the tooth that protrudes from the gum, and is normally the only visible part of the tooth. The root is the portion of the tooth embedded in the gum and bone. The entire tooth root is surrounded by the periodontal membrane, also known as the periodontal ligament. The periodontal membrane is a soft, ligamentous material which connects the tooth to its bony socket. The periodontal membrane surrounds the entire root, but does not extend onto the crown.

If the periodontal membrane of an exarticulated tooth has not been substantially damaged, and if its cells are still alive, the tooth can be successfully reimplanted in its socket. After several days, the tooth will become naturally reaffixed to the socket. But if the cells of the membrane have died, the tooth is lost.

It has been known that, if an exarticulated tooth is stored in a proper medium, its periodontal membrane can be preserved, and the tooth can be saved. Various experiments have been done to determine which media are best for storing an exarticulated tooth. One article describing such experiments is "Milk and Saliva as Possible Storage Media for Traumatically Exarticulated Teeth Prior to Replantation", by L. Blomlof, Swedish Dental Journal, vol. 5, Supp. No. 8, pages 1-26 (1981). As indicated by the title, the article describes experiments which tested the effectiveness of milk and saliva as storage media for exarticulated monkey teeth. Both of these naturally-occurring media were found to be effective in promoting the vitality of the cells of the periodontal membrane.

The above-cited article also reports the results of experiments with artificial storage media. The medium that performed best in most of the experiments is the solution known as "Eagle's medium". Eagle's medium was first described in the article by M. Eagle, entitled "Amino acid metabolism in mammalian cell cultures", in Science, vol. 130, pages 432-437 (1959). Eagle's medium has been modified by others, and is available commercially from various sources.

The other artificial medium which has been shown effective in preserving an exarticulated tooth is the Hanks Balanced Salt Solution. This solution was also used successfully in the experiments reported in the above-cited article.

Other experiments on the preservation of monkey teeth in Eagle's medium have been reported in "Periodontal and Pulpal Healing of Monkey Incisors Preserved in Tissue Culture Before Replantation", by J. O. Andreasen et al, in the International Journal of Oral Surgery, vol. 7, pages 104-112 (1978). And the Hanks solution has been further tested, and found to be effective, in experiments reported in the article by L. Blomlof et al, entitled "Effect of Storage in Media with Different Ion Strength and Osmolalities on Human Periodontal Ligament Cells", in the Scandinavian Journal of Dental Research, vol. 89, pages 180-7 (1981).

In theory, it is thus comparatively easy to preserve an exarticulated tooth, and then to reimplant it. Unfortunately, exarticulation of a tooth is a traumatic experience for the victim. If the victim is a child, the trauma can be equally severe for the parent. Neither parents nor children are ordinarily well-informed about how to preserve a tooth in this kind of emergency. Very often, by the time the tooth has been carried to a dentist, the cells of the periodontal membrane have died, and it is too late to save the tooth.

The present invention provides a simple method for saving an exarticulated tooth, and also provides an apparatus which is especially useful in practicing the method. The invention makes it possible for the general public to apply the above-described scientific findings for practical benefit.

SUMMARY OF THE INVENTION

According to the invention, an exarticulated tooth is picked up by its crown, so as not to harm the periodontal membrane. The tooth is then dropped into a net, the net being attached to a rigid, or semi-rigid, basket. The basket rests in a container of a modified saline solution which tends to enhance the vitality of the cells of the periodontal membrane.

In one embodiment, the lid of the container has a sponge means on its interior surface. The lid is screwed onto the container, and the tooth and patient are transported to the nearest dentist. The dentist opens the container, and places the lid on a working surface, so that the sponge means faces upward. The dentist then lifts the basket, with the net, from the solution, and inverts the net so that the tooth falls out onto the sponge means. The tooth is then gripped with a forceps, or other suitable tool, and reimplanted into its socket.

The basket can be constructed of metal or plastic, and is preferably equipped with a pair of handles which facilitate the lifting of the basket out of the solution. The solution is preferably a modified saline solution, such as a Hanks' Balanced Salt Solution or an Eagle's medium.

In an alternative embodiment, the basket and net are omitted. Instead, the container is lined with a padded material to cushion the tooth. The padded material can assume the form of bubbles of air or liquid, or it can be a sponge material covering the entire interior surface of the container.

In another alternative embodiment, the net is present but the basket is omitted. The net remains affixed to the container at all times.

In still another embodiment, there is a basket and a net, as described above, but the solution is initially stored in a bag located within the lid of the container. A set of knife edges are mounted on the basket, and are oriented so as to puncture the bag when the lid is unscrewed.

In yet another embodiment, there is no net and no basket. Instead the tooth is stored within a pouch made of a water-impermeable material. The pouch includes a flap, or equivalent means, which can fold over the opening of the pouch, and which effectively seals the tooth from the outside environment until dental aid is available.

It is therefore an object to provide a method for saving an exarticulated tooth.

It is another object of the invention to provide a method for storing the exarticulated tooth, and transporting it to a dentist.

It is another object of the invention to provide apparatus which facilitates the practice of the method described above.

It is another object to provide a basket and net structure which is especially adapted for use in storing and transporting an exarticulated tooth.

It is another object to provide apparatus which can be used with commercially available media for storing and transporting exarticulated teeth.

It is another object to provide alternative structures for practicing the method of the invention.

Other objects and advantages of the invention will be apparent to those skilled in the art, from a reading of the following brief description of the drawings, the detailed description of the invention, an the appended claims.

DETAILED DESCRIPTION OF THE INVENTION

The present invention provides a simple method and apparatus for saving a tooth that has been exarticulated, or suddenly and completely knocked out of the patient's mouth.

Figures 4, 5:
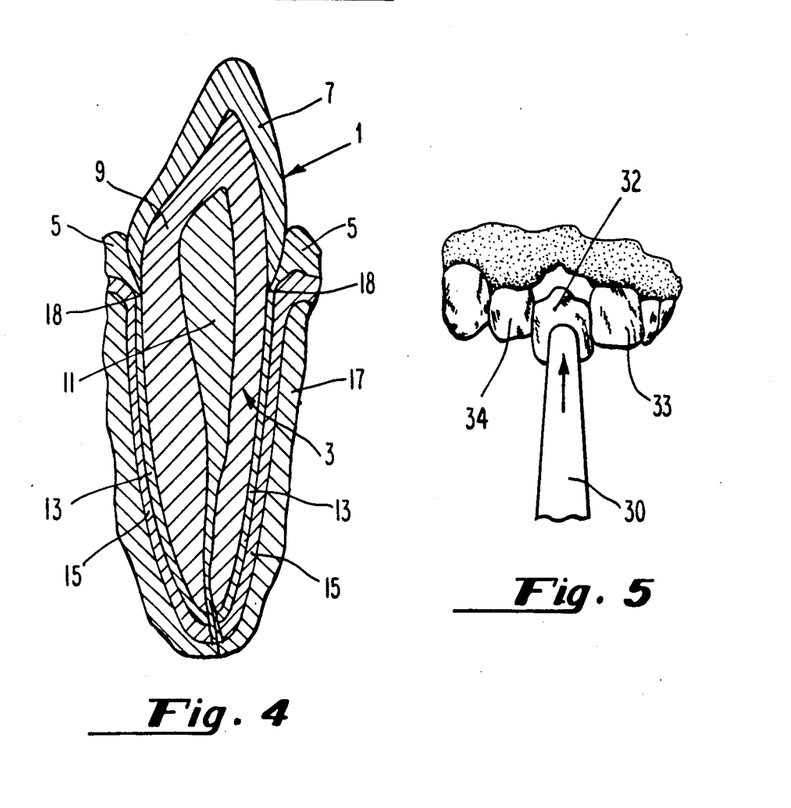
FIG. 4 is a diagram of the components of a tooth.
FIG. 5 is a diagram illustrating the reimplantation of a tooth into a patient's mouth.

In order to understand the invention, it is helpful to review the anatomy of a tooth. FIG. 4 is a diagram showing, in cross-section, the principal components of a single-rooted tooth. The tooth has a crown portion, designated generally by reference numeral 1, and a root portion, designated generally by reference numeral 3. The crown is the portion of the tooth which protrudes from the gingiva (or gum) 5.

The crown portion has a coating of enamel 7, under which is located a layer of dentin 9, a tubular structure which supports the enamel and provides a sensory mechanism. Pulp chamber 11 contains the nerve of the tooth. The outer covering of the root of the tooth is known as the cementum, and is designated by reference numeral 13. The periodontal membrane 15, also known as the periodontal ligament or PDL, is disposed between the cementum 13 and the bony socket 17 in which the tooth rests.

The location at which the enamel 7 abuts the cementum 13 is known as the cemento-enamel junction, and is designated by reference numeral 18. Roughly speaking, the cemento-enamel junction is the portion of the tooth where the tooth crown meets the tooth root.

The tooth shown in FIG. 4 is a single-rooted tooth. Other teeth, such as molars, have two roots, which are connected to each other. The structure of single-rooted and double-rooted teeth is otherwise the same as shown in FIG. 4.

When a tooth is exarticulated, or knocked out, the periodontal membrane generally remains with the tooth. If this membrane is undamaged, it is possible to reimplant the tooth in its socket, and, after a few days, the tooth will become firmly and naturally reattached.

Figure 1:
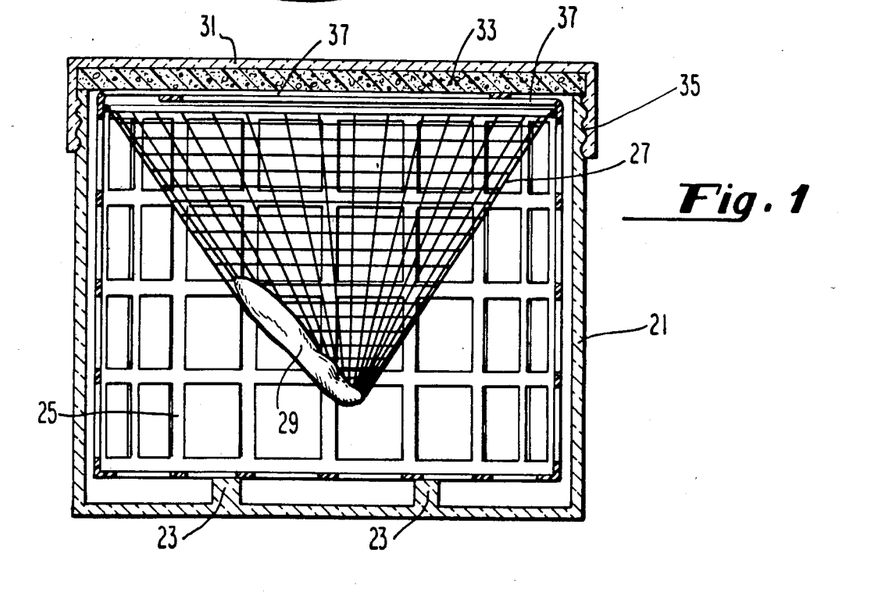
FIG. 1 is a cross-sectional view of the container for storing a tooth, having a basket and net, constructed according to one embodiment of the present invention.
Figure 2:
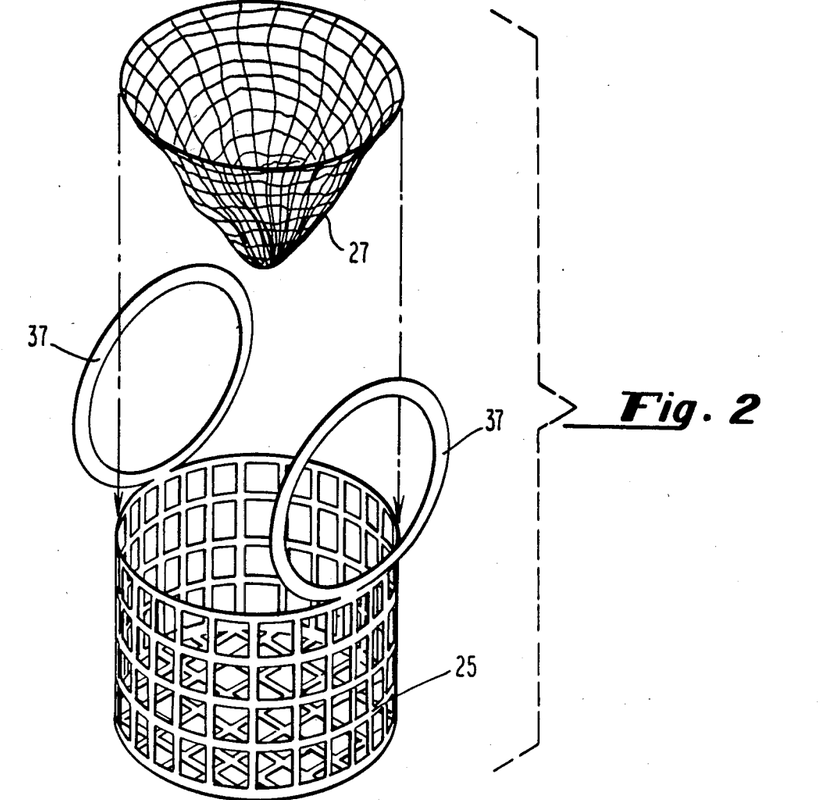
FIG. 2 is an exploded perspective view of the apparatus of FIG. 1, showing both the basket, and the net attached to the basket.
Figure 3:
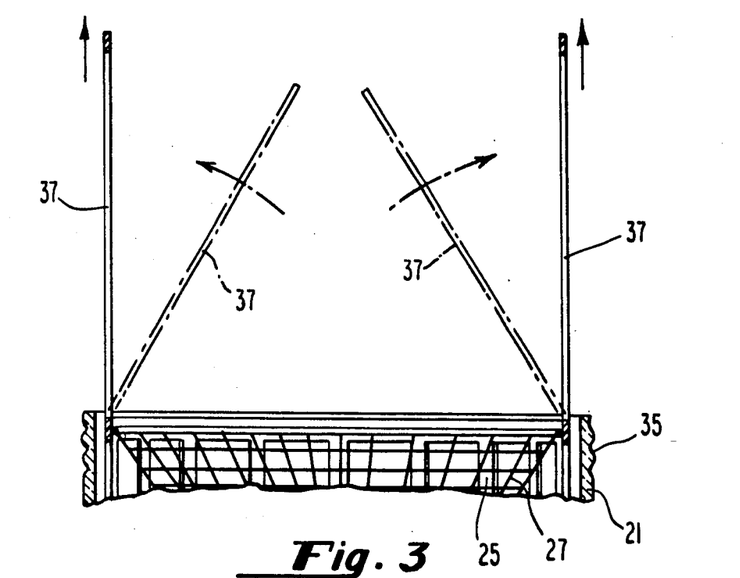
FIG. 3 is a fragmentary cross-sectional view of the apparatus shown in FIGS. 1 and 2, showing the structure of the handles by which the basket can be lifted from the container.

One embodiment of the apparatus of the present invention is shown in FIGS. 1-3. The apparatus comprises container 21, which can be a jar or bottle. Disposed within container 21 is basket 25 which rests on feet 23. Feet 23 can be integrally formed with the container, as shown, or they can be made part of the basket. The basket can be of wire mesh construction, or it can be formed of plastic. Attached to basket 25 is net 27, which can be made of nylon, or of other flexible material. The size of the net is such that it encloses a volume less than that of the container. FIG. 1 shows tooth 29 resting within net 27. For the sake of clarity, no fluid is shown in the container, in FIG. 1, but it is understood that, when the container is used to store a tooth, the interior of the container will be filled with a solution which tends to promote the vitality of the cells of the periodontal membrane.

Container 21 is closed off with lid 31. Mounted on the interior surface of lid 31 is sponge 33. The "interior surface" means the surface which is inside the container when the lid is attached to the container. The sponge helps to seal the contents of the container, although this seal need not be especially tight. The sponge has a more specific function, in the invention, as will be described below. Lid 31 is screwed onto the container, by threads 35.

A pair of handles 37, more plainly visible in the exploded perspective view of FIG. 2, are attached to the basket 25. The handles are used to lift the basket from the container. The handles shown in the figures are of the form of generally circular rings, and are pivotably attached to the periphery of the basket. The rings can be folded over each other while the lid is screwed onto the container. FIG. 1 shows handles 37 in this fully folded-down position. The view of FIG. 3 shows the movement of handles 37, as they are being opened, so as to lift the basket.

One embodiment of the method of the present invention can now be described. First, the exarticulated tooth is picked up from the ground. In grasping the tooth, it is preferable to touch only the crown portion (reference numeral 7 in FIG. 4), and not the periodontal membrane 15.

Lid 31 of container 21 is then unscrewed. The container is filled with a modified saline solution, as described below. It is possible to store the solution separately from the container, and to pour the solution into the container when needed. It may be more convenient to store the solution permanently in the container.

The tooth is dropped into the net, and into the solution. The container lid is reaffixed to the container. The container and the patient are then brought to a dentist as quickly as possible. The tooth remains gently suspended in the solution. Because the volume of the net is smaller than that of the basket, the tooth is unlikely to collide with the walls of the basket while being transported.

When the patient arrives at the dentist's office, with the container and the tooth, the dentist unscrews the lid, and places it on a flat working surface, so that the sponge faces upward. The dentist then lifts the basket, by its handles, out of the container and the solution. The basket, with the net still attached, is then gently inverted, so that the tooth falls out onto the sponge. The dentist takes a tooth extraction forceps, as illustrated by reference numeral 30 in FIG. 5, or any other equivalent implement, and gently grips the tooth 32 by its crown portion so that the tips of the forceps extend no further than the level of the cemento-enamel junction, with the apex of the root facing away from the forceps. The dentist carries the tooth, in the forceps, to the patient, who has been anesthetized, and reimplants the tooth in its socket.

The above-described method can be practiced in two variations. In one variation, the container lid is placed over the basket, and when the basket is inverted, the tooth falls onto the sponge. The basket is then lifted away from the lid, and the tooth thus remains on the sponge. In another variation, the dentist places the lid on a working surface, and then inverts the basket so that the tooth falls onto the sponge. Either variation is within the scope of the invention.

FIG. 5 shows the tooth 32 being reimplanted, between teeth 33 and 34, by forceps 30. If the periodontal membrane has not been damaged during storage and transportation, the tooth will reattach itself naturally to the socket in about 2–3 days, and the healing process is usually complete in about two weeks.

Figure 6:
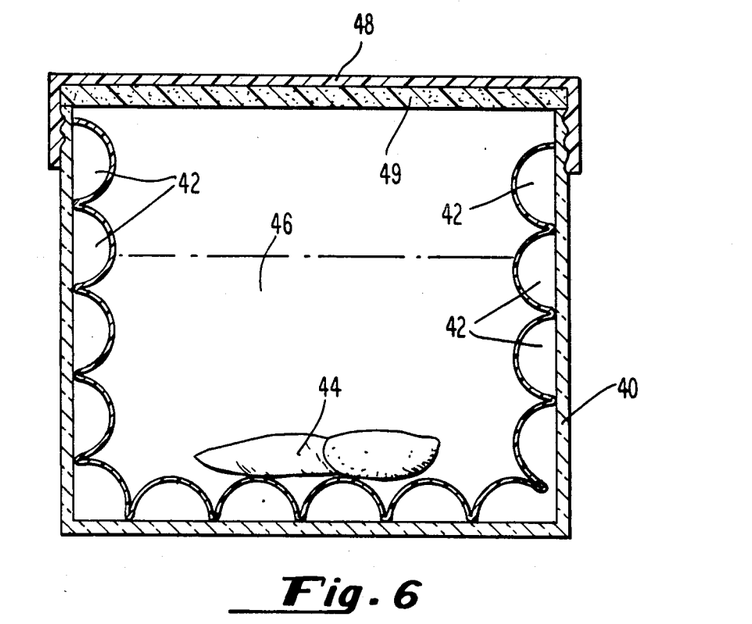
FIG. 6 is a cross-sectional view, similar to FIG. 1, showing an alternative embodiment of the invention, wherein the net and basket are omitted, and wherein the container is padded with fluid-filled bubbles.

FIGS. 6–10 show alternative embodiments of the invention. FIG. 6 is a cross-sectional view, similar to that of FIG. 1, of an apparatus in which the basket and the net are omitted. Instead, the interior of container 40 is lined with fluid-filled bubbles 42. Tooth 44 rests on these bubbles, while immersed in solution 46. Lid 48 and sponge 49 are similar to the lid and sponge of FIG. 1. The bubbles define a soft, flexible surface, protecting the tooth while it is being transported. The bubbles could also be filled with a solid material, such as a powder, and would still provide the needed flexibility.

In use, the apparatus of FIG. 6 is first filled with the tooth-preserving solution. The exarticulated tooth is dropped into the container, and the lid is screwed on. To remove the tooth, the dentist unscrews the lid, and gently pours the solution out, until the tooth can be easily grasped. Alternatively, the dentist can reach into the solution and pick up the tooth immediately.

Figure 7:
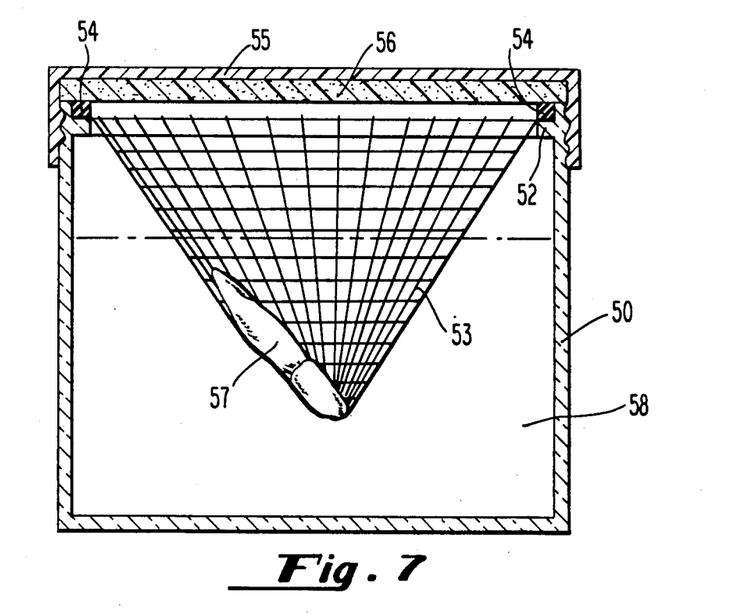
FIG. 7 is a cross-sectional view of another embodiment of the invention, wherein the basket is omitted, and wherein the net is permanently affixed to the container.

FIG. 7 shows another alternative embodiment wherein there is a net but no basket. Container 50 is integrally formed with flange 52. Net 53 is attached to ring 54 which rests on the flange, and which fits tightly within the container. Lid 55 and sponge 56 are similar to the lid and sponge in the embodiments described above. Tooth 57 is placed in net 53, and the net is at least partially immersed in solution 58.

In use, the apparatus of FIG. 7 is first unscrewed and the tooth is dropped into the net. The tooth falls to the bottom of the net, and is therefore immersed in the solution. The dentist can then manually remove the tooth from the net, either before or after pouring the solution out. Alternatively, the methods for removing the tooth from the container, described above, can be used. The net is intended to remain fixed to the container. In the embodiment shown, the net is affixed by friction, i.e. The outside diameter of ring 54 is almost equal to the inside diameter of the part of the container that holds the ring. Flange 52 need not be integrally formed, but could be separately made and attached to the container.

Figure 8:
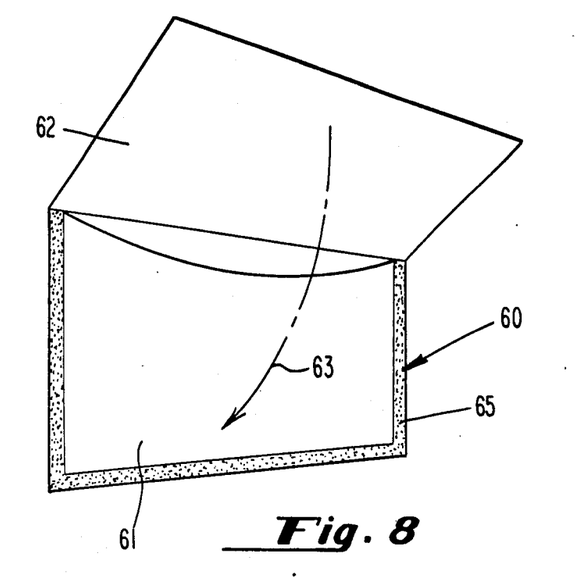
FIG. 8 is a cross-sectional view of another embodiment of the invention, showing a moisture-impermeable pouch for storing the tooth.

FIG. 8 shows another apparatus for preserving a tooth. This structure is a pouch or envelope 60, preferably made of a liquid-impermeable material. The pouch includes a body 61 and a flap 62. The flap folds over, as shown by arrow 63. The body is lined with a sealing means 65, which is shown as an adhesive material. The adhesive could also be disposed on the flap. Many other sealing means are possible instead of an adhesive. The pouch could be constructed with a zipper-like device which forms a closure between the flap and the body. All such means of sealing the flap to the pouch body are to be considered within the scope of the invention.

To use the pouch of FIG. 8, the flap is opened and the exarticulated tooth is placed inside. The flap is folded over and sealed to the body portion. Note that there is no solution in the pouch. It has been found that if a tooth is tightly wrapped in a liquid-impermeable material, the periodontal membrane can be preserved for some time, and it is still possible to save the tooth. When the patient arrives at the dentist's office, the dentist simply opens the flap, removes the tooth, and reimplants it in the manner described above.

Figure 9:
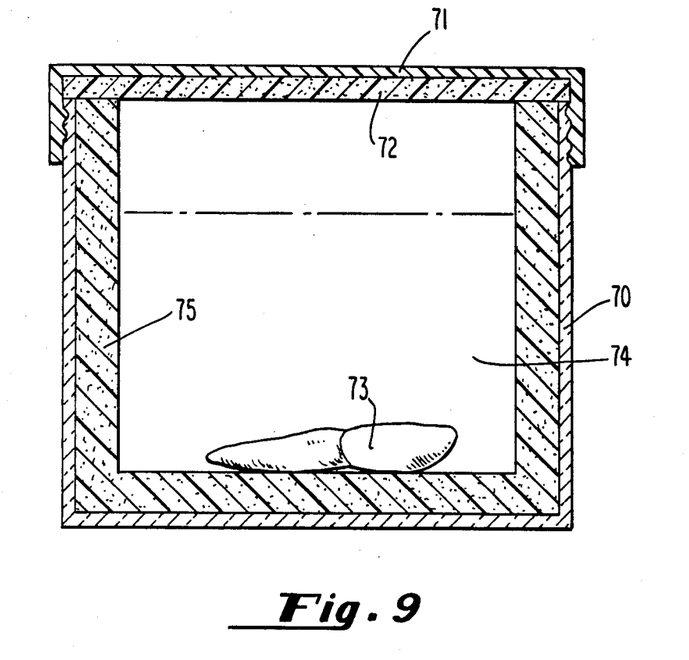
FIG. 9 is a cross-sectional view of another embodiment of the invention, wherein the net and basket are omitted, and wherein the container is lined with a flexible material.

FIG. 9 shows another embodiment of the invention. This embodiment is similar to that of FIG. 6. The apparatus includes container 70, lid 71, and sponge 72, as in the embodiments of FIGS. 1, 6, and 7. The figure also shows tooth 73 immersed in solution 74. In FIG. 9, however, the interior of container 70 is lined with a flexible material 75. This material can be another sponge, or it can be rubber, or any other equivalent substance. The material 75 covers substantially all of the interior surface of the container, although the cushioning effect is most important at the bottom. The apparatus of FIG. 9 is used in substantially the same manner as that of FIG. 6.

Figure 10:
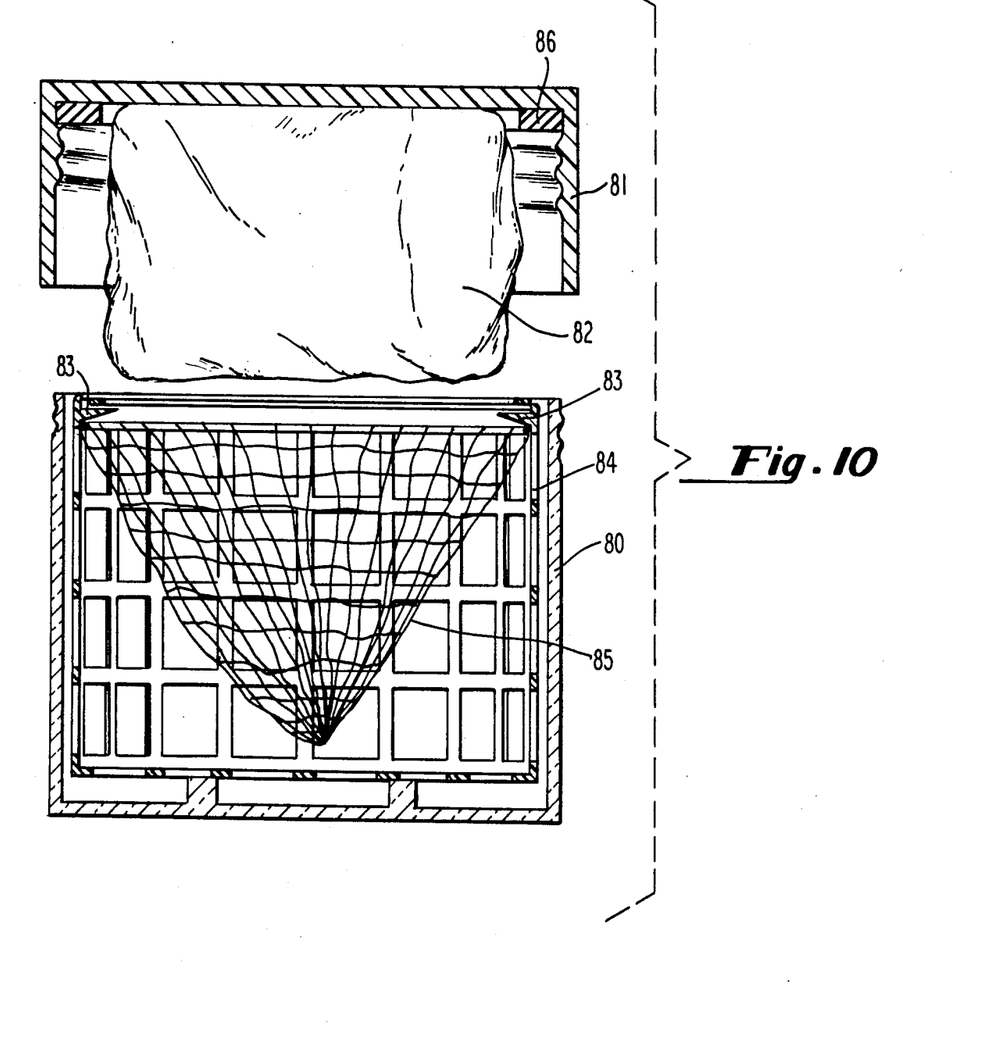
FIG. 10 is an exploded cross-sectional view of another embodiment of the invention, wherein the tooth-preserving solution is stored in a bag held within the lid of the container.

FIG. 10 shows another embodiment of the apparatus of the invention. The apparatus includes container 80 and lid 81. The lid screws onto the container, as in FIG. 1, but the lid is made large enough to hold bag 82 in which the tooth-preserving solution is stored. Knife edges 83, attached to basket 84, are disposed to puncture the bag when the bag is turned in one direction.

The knife edges are preferably oriented so that the bag is punctured as the lid is unscrewed, i.e. when the apparatus is about to be first used.

Net 85 rests within the basket, as in the embodiment of FIG. 1. Gasket 86 seals the lid to the container when the two are screwed together. The gasket can be made of rubber, or it can be a sponge, or other flexible material.

In use, the apparatus of FIG. 10 is stored with the solution contained within the bag. When it is necessary to place a tooth within the container, the lid is unscrewed, causing the bag to tear, and releasing the solution into the container. The apparatus is then used in the same manner as that of FIG. 1, except that the device lacks a sponge which covers the entire interior surface of the lid.

When the tooth is reimplanted, one needs a retaining means (not shown in the drawings) to hold the tooth in place. There are many well-known ways of retaining the tooth. One way is to attach brackets and wires to the teeth, which hold the reimplanted tooth while allowing the tooth some movement. Another method is to use a bonding material, of the type commonly used to fill chipped teeth and the like, to connect the reimplanted tooth to its neighbors. The bonding material allows the tooth to move somewhat. After the healing process is complete, the bonding material can be removed.

The only unacceptable means of retaining the reimplanted tooth is the use of a rigid bar which prevents any movement of the reimplanted tooth. Such a rigid retaining means can cause ankylosis, a condition in which the bone around the tooth becomes connected directly to the dentin, and the periodontal membrane is entirely lost.

As stated above, two preferred solutions for use in the container are the so-called Hanks' Balanced Salt Solutions, and Eagle's medium. Both of these media are are commercially available from Gibco Laboratories of Grand Island, N.Y., and from other sources.

The Hanks solutions contain a mixture of various inorganic salts, plus certain other components. The salts found in several variations of the Hanks solutions are shown in the following table.

| Component: | Concentration in g/l Solution No.: | | | | |
| --- | --- | --- | --- | --- | --- |
| | 1 | 2 | 3 | 4 | 5 |
| $CaCl_2$ (anhyd.) | 0.14 | 0 | 1.40 | 0 | 0.14 |
| KCl | 0.40 | 0.40 | 4.00 | 4.00 | 0.40 |
| $KH_2PO_4$ | 0.06 | 0.06 | 0.60 | 0.60 | 0.06 |
| $MgCl_2.6H_2O$ | 0.10 | 0 | 1.00 | 0 | 0 |
| $MgSO_4$ (anhyd.) | 0 | 0 | 0 | 0 | 0.0977 |
| $MgSO_4.7H_2O$ | 0.10 | 0 | 1.00 | 0 | 0 |
| NaCl | 8.00 | 8.00 | 80.00 | 80.00 | 8.00 |
| $NaHCO_3$ | 0.35 | 0.35 | 0 | 0 | 0 |
| $Na_2HPO_4$ | 0 | 0 | 0 | 0 | 0.048 |
| $Na_2HPO_4.7H_2O$ | 0.09 | 0.09 | 0.90 | 0.90 | 0 |

The Hanks solutions also contain a certain amount of glucose, to provide nutrition for the cells stored in the solution, and may also contain a coloring agent.

Solutions Nos. 3 and 4 can be described as more concentrated versions of Solutions Nos. 1 and 2.

Eagle's medium, in its modified forms, includes inorganic salts of the types shown in the above table, plus vitamins, amino acids, and antibiotics. More specifically, the amino acids which are used in the Eagle's medium available from Gibco Laboratories include L-Arginine, L-Cystine, L-Glutamine, L-Histidien, L-Isoleucine, L-Leucine, L-Lysine, L-Methionine, L-Phenylalanine, L-Threonine, L-Tryptophane, L-Tyrosine, and L-Valine. The vitamins used in the Eagle's medium sold by Gibco include biotin, D-Ca pantothenate, choline chloride, folic acid, I-inositol, nicotinamide, pyridoxal HCl, riboflavin, and thiamine HCl. In the experiments reported in the article by Blomlof in the Swedish Dental Journal, cited above, the Eagle's medium was augmented by calf serum.

A major purpose of the Hanks solution, or Eagle's medium, or any other type of artificial solution used to store a tooth, is to provide a composition which most nearly duplicates that of the fluid in the cells being preserved. If the tooth is stored in a solution which does not match the composition of the cell contents, there will be a net inflow or outflow of ions across the boundary of the cell. This ion transport can destroy the cell. In fact, if the tooth is placed in pure water, the difference in ion concentration between the interior and exterior of the outer cells on the periodontal membrane will cause those cells to explode, thereby killing them.

Because water can kill the cells of the periodontal membrane, it is not recommended that the tooth be rinsed with water before reimplantation. Moreover, the tooth will be rinsed automatically when it is stored and transported in one of the solutions described above.

The Hanks solutions and Eagle's medium have been shown to be particularly effective in preserving the vitality of the cells of the periodontal membrane. Indeed, the experiments with Eagle's medium suggest that it is possible to store exarticulated teeth in that medium for several days without damage to the membrane. The Hanks solution appears to be effective for several hours, but it may have the advantage of a longer shelf life than Eagle's medium.

It is quite possible that other artificial solutions can be used instead of the solutions mentioned above. There are many other such solutions, which are commercially available, and which have been developed for use by research laboratories for the purpose of preservation of various natural tissues. Examples include the so-called Gey's Balanced Salt Solution and Puck's Saline. However, the latter solutions are not believed to have been tested with exarticulated teeth.

The specific embodiments described above should be considered exemplary, and not limiting. The invention can be further modified in many ways, within the scope of the disclosure. The invention is not limited to the materials cited above, or to the particular tooth-preserving solutions described. These and other similar modifications should be considered within the spirit and scope of the following claims.

What is claimed is:

1. A method of preserving an exarticulated tooth, comprising the steps of:
   (a) placing the tooth in a container, the container having a cushioning means on its interior, at least part of the cushioning means comprising a non-liquid material attached to the container, the container being substantially filled with a solution,
   (b) storing the tooth in the container, in the solution, until dental said is available,
   (c) removing the tooth from the container, and
   (d) reimplanting the tooth.

2. The method of claim 1, wherein the container has lid, and wherein at least part of the cushioning means is disposed on the interior surface of the lid, and wherein the removing step comprises the step of orienting the lid so that its cushioning means faces upward, and tilting the container so as to allow the tooth to fall onto the cushioning means on the lid.

3. A method of preserving an exarticulated tooth, comprising the steps of:
(a) placing the tooth in a pouch, the pouch being substantially impermeable to liquids, the pouch defining an interior portion, the interior portion of the pouch being substantially free of liquid,
(b) storing the tooth in the pouch until dental aid is available,
(c) removing the tooth from the pouch, and
(d) reimplanting the tooth.

4. Apparatus for preserving an exarticulated toot, comprising:
(a) a container means, the container means having a solution capable of preserving a tooth,
(b) a basket means, the basket means being removably inserted into the container means, and
(c) a net means, the net means being attached to the basket means, the net means having a mesh size sufficient to hold the tooth in the net means.

5. The apparatus of claim 4, wherein the container means has an interior surface, and wherein at least part of the interior surface is provided with as cushioning material.

6. The apparatus of claim 5, wherein the cushioning material is a sponge material.

7. The apparatus of claim 5, wherein the cushioning material comprises a plurality of fluid-filed bubbles.

8. Apparatus for preserving an exarticulated tooth, comprising a container means and net means, the net means being attached to the container means, the net means having a mesh size sufficient to hold the tooth in the net means, the container means having a solution which is capable of preserving a tooth, the container means being sufficiently filled with said solution such that a tooth disposed within the net means will be immersed in the solution when the net means is inserted into the container means.

9. The apparatus of claim 8, the container having a lid, wherein the lid has an interior surface, and wherein there is a sponge means disposed on the interior surface of the lid.

10. Apparatus for preserving an exarticulated tooth, comprising:
(a) a container means, the container means having a lid which is attached to the container means, the container means holding a solution which is capable of preserving a tooth,
(b) bag means, disposed within the lid, the bag means being capable of being filled with a solution,
(c) a basket means, sized for insertion into the container means, and
(d) a net means, the net means being attached to the basket means, the net means having a mesh size sufficient to hold the tooth in the net means, and
(e) knife edge means, mounted on the basket means, and positioned to break the bag means when the lid is rotated.

11. A method of preserving an exarticulated tooth, comprising the steps of:
(a) placing the tooth in a container, the container having a cushioning means disposed within its interior, the container being substantially filled with a solution, the container having a lid, the lid comprising means for storing a bag of liquid, the container also having means for puncturing said bag,
(b) operating the puncturing means so as to cause the liquid to flow towards the bottom of the container,
(b) storing the tooth in the container, in the solution, until dental aid is available,
(c) removing the tooth from the container, and
(d) reimplanting the tooth.

12. The method of claim 11, wherein the puncturing means comprises at least one knife edge, and wherein the operating step comprises rotating the lid so as to cause the bag to engage the knife edge.

13. Apparatus for preserving an exarticulated tooth, comprising a container means and a holding means, disposed within the container means, the holding means comprising means for holding the tooth within the container, and for preventing the tooth from contacting the walls of the container means, the container means having a solution which is capable of preserving a tooth, the container means being sufficiently filled with said solution such that a tooth disposed within the holding means will be immersed in the solution when the holding means is inserted into the container means.

14. The apparatus of claim 13, wherein the holding means includes a basket disposed within the container.

15. The apparatus of claim 13, wherein the holding means includes a net disposed within the container, the net being of sufficient mesh size to hold the tooth within the net.

16. A method of preserving an exarticulated tooth, comprising the steps of:
(a) placing the tooth in a container, the container having a cushioning means on its interior, the container being substantially filled with a solution,
(b) storing the tooth in the container, in the solution, until dental said is available,
(c) removing the tooth from the container, and
(d) reimplanting the tooth, wherein the container has a lid, and wherein at least part of the cushioning means is disposed on the interior surface of the lid, and wherein the removing step comprises the step of orienting the lid so that its cushioning means faces upward, and tilting the container so as to allow the tooth to fall onto the cushioning means on the lid.

* * * * *